US007068369B2

(12) United States Patent
Lee et al.

(10) Patent No.: US 7,068,369 B2
(45) Date of Patent: Jun. 27, 2006

(54) APPARATUS FOR MEASURING FRUIT PROPERTIES INCLUDING A FUNCTION FOR AUTOMATICALLY CONTROLLING THE INTENSITY OF LIGHT FROM A LIGHT SOURCE

(75) Inventors: Kang Jin Lee, Suwon (KR); Kyu Hong Choi, Suwon (KR); Dong Soo Choi, Suwon (KR); Soo Jang Lee, Suwon (KR); Ki Woo Lee, Daegu (KR)

(73) Assignee: Rural Development Administration, Gyeonggi-do (KR)

( * ) Notice: Subject to any disclaimer, the term of this patent is extended or adjusted under 35 U.S.C. 154(b) by 328 days.

(21) Appl. No.: 10/484,692

(22) PCT Filed: Oct. 26, 2001

(86) PCT No.: PCT/KR01/01810

§ 371 (c)(1),
(2), (4) Date: Jan. 26, 2004

(87) PCT Pub. No.: WO03/010520

PCT Pub. Date: Feb. 6, 2003

(65) Prior Publication Data

US 2005/0004771 A1    Jan. 6, 2005

(30) Foreign Application Priority Data

Jul. 24, 2001    (KR) ............................... 2001-44464

(51) Int. Cl.
*G01J 3/28* (2006.01)
(52) U.S. Cl. ...................... 356/326; 356/432; 209/588; 250/910

(58) Field of Classification Search ................ 356/303; 250/910, 339.06, 339.07, 339.11, 339.12; 209/581, 577, 582, 588
See application file for complete search history.

(56) References Cited

U.S. PATENT DOCUMENTS 6,233,051 B1 * 5/2001 Kimura et al. ............... 356/433

FOREIGN PATENT DOCUMENTS

EP    0 939 316    9/1999

(Continued)

*Primary Examiner*—Gregory Toatley
*Assistant Examiner*—Marissa J Detschel
(74) *Attorney, Agent, or Firm*—Jacobson Holman PLLC

(57) ABSTRACT

An apparatus for measuring fruit properties, in order to classify fruit according to internal qualities, measures the sweetness of a fruit sample using near-infrared spectroscopy. The apparatus includes a pair of waveguides (12), a pair of optic emitter/sensor assemblies (14), a light-interrupting unit (20), and a light detector (40). The light detector calculates the intensity of light, transmitted from a light source and received by the optical emitter/sensor assemblies, thus allowing spectral analysis and interpretation for the determination of sweetness and acidity of a variety of fruits. The light detector controls the light-interrupting unit to interrupt the optical path when the light intensity is reduced. The apparatus is suitable for use in an automated line, for effective and reliable measurement of internal fruit properties, to improve operational efficiency and precision in fruit selection.

2 Claims, 3 Drawing Sheets

FOREIGN PATENT DOCUMENTS

| | | |
|---|---|---|
| EP | 0 957 353 | 11/1999 |
| EP | 0 961 112 | 12/1999 |
| JP | 1-216265 | 8/1989 |
| JP | 8-152401 | 6/1996 |
| JP | 10-62341 | 3/1998 |
| JP | 2000-11473 | 4/2000 |
| JP | 2001-29706 | 2/2001 |
| WO | WO 99/34193 | 7/1999 |

* cited by examiner

APPARATUS FOR MEASURING FRUIT PROPERTIES INCLUDING A FUNCTION FOR AUTOMATICALLY CONTROLLING THE INTENSITY OF LIGHT FROM A LIGHT SOURCE

This is a nationalization of PCT/KR01/01810 filed Oct. 26, 2001 and published in English.

TECHNICAL FIELD

The present invention relates in general to an apparatus for measuring fruit properties, and more particularly to an apparatus for measuring the internal quality of a fruit sample, including a function for automatically controlling the intensity of light from a light source, using near-infrared spectroscopy to classify fruit according to sugar content and acidity.

BACKGROUND ART

As well known to those skilled in the art, the sugar content (sweetness) of a given fruit is typically determined by experienced workers relying upon their senses of sight, touch, and smell. This process, which is based on the subjectivity of individual workers, is inherently inconsistent and inaccurate, thus reducing the reliability of fruit quality claims and rendering impossible the reliable selection of fruit according to a grade of sweetness. It takes several years for a worker to attain an acceptable level of competence to gauge the sweetness of a given type of fruit.

In an attempt to solve these problems, near-infrared spectroscopy has been used, with which internal qualities of fruit, such as sweetness or acidity, can be precisely determined. An operator positions in a light path a fruit sample selected from target fruits, and the intensity of light emitted from a near-infrared light source is sensed with respect to the positioned fruit, to determine a deflection value and a transmission value and thereby grade individual pieces of fruit according to sugar content. Here, the deflection value is the ratio of the intensity of light from the light source relative to the intensity of light deflected by the fruit sample, and the transmission value is the ratio of the intensity of light from the light source relative to the intensity of deflected light, and the transmission is a ratio of the intensity of light from a light source relative to the intensity of transmitted light. Preferably, the light source maintains a constant intensity of light, irrespective of the passage of time.

However, output of the light source used for measuring the sweetness of fruits is reduced as time passes while it is in operation, and accordingly, the error in measuring the sweetness increases as time passes. To reduce the error in measurement, light is radiated from a light source to a reference sample (compressed solid block of barium sulfide or Teflon) for measurement of light transmission or deflection at time intervals of one hour, and the energy of light transmitted through or deflected by the sample is set as the intensity of the light source. However, this method needs an additional step of measuring the light energy transmitted through or deflected by such a reference sample at regular time intervals, thus causing an inconvenience in operation.

In addition, the internal qualities such as sweetness or acidity of a fruit vary even within the same fruit according to portions thereof, that is, top and bottom, left and right portions, etc., and thus, it is difficult to precisely judge the internal qualities of fruits.

DISCLOSURE OF THE INVENTION

Therefore, the present invention has been made in view of the above problems, and it is an object of the present invention to provide an apparatus for measuring internal qualities of fruits, which controls the intensity of light from a light source by radiating near infrared rays to opposite sides of a fruit sample, measuring and analyzing the light energy deflected by the fruit, and correcting a high level reference value and a low level reference value of the intensity of the light energy every when the intensity of the light energy is reduced, thereby reducing the error in judgment of the sweetness of fruits caused by a reduction in the intensity of the light energy and improving the accuracy of selection of fruits based on the internal qualities of the fruits.

In accordance with the present invention, the above and other objects can be accomplished by a provision of an apparatus for measuring internal qualities of fruits with a function of automatically controlling the intensity of light from a light source, comprising: light guiding parts to guide light radiated from the light source to a position of a fruit sample to be measured; a light radiating and receiving assembly to radiate the light transmitted through the light guiding parts placed at a position near the fruit sample to fresh of the fruit sample so that the light is dispersed by the fresh of the fruit sample, and to receive the light deflected by the fresh of the fruit sample; a light interrupting unit installed between the light guiding parts coupled to the light radiating and receiving assembly which receives the light deflected by the fresh of the fruit sample, so as to selectively interrupt an optical path of the light deflected by the fresh of the fruit sample; and a light detector to calculate the intensity of light, radiated from the light source and received by the light radiating and receiving assembly, thus allowing analysis and interpretation of a spectrum for determination of sweetness and acidity of fruits, the light detector setting a detected signal, which is detected without any fruit sample, as a high level reference signal, and controlling the light interrupting unit to interrupt an optical path of light from the light source, thus setting a low level reference signal, when the intensity of the received light varies gradually.

In the above apparatus, the light interrupting unit is comprised of: a solenoid actuator operated with a power of 12V to repeatedly move at a predetermined rotational angle; a light interrupting board operated in conjunction with the solenoid actuator to selectively interrupt light from the light source or allow the light to pass through the optical path; a casing housing both the solenoid actuator and the light interrupting board; a power terminal provided outside the casing and applying electric power of 12V to the solenoid actuator; and a second light guiding part coupled to the casing, one side of which is exposed with an optical fiber so as to interrupt the light with the light interrupting board, and directing the light passing through it to the light detector.

BRIEF DESCRIPTION OF THE DRAWINGS

The above and other objects, features and other advantages of the present invention will be more clearly understood from the following detailed description taken in conjunction with the accompanying drawings, in which:

FIG. 2b is a side sectional view of the light interrupting unit of FIG. 2a;

FIG. 3b is a side sectional view of the light interrupting unit of FIG. 3a.

BEST MODE FOR CARRYING OUT THE INVENTION

The apparatus for measuring internal qualities of fruits with a function of controlling the intensity of light from a light source according to the present invention will be described in detail with reference to the accompanying drawings.

Figure 1:
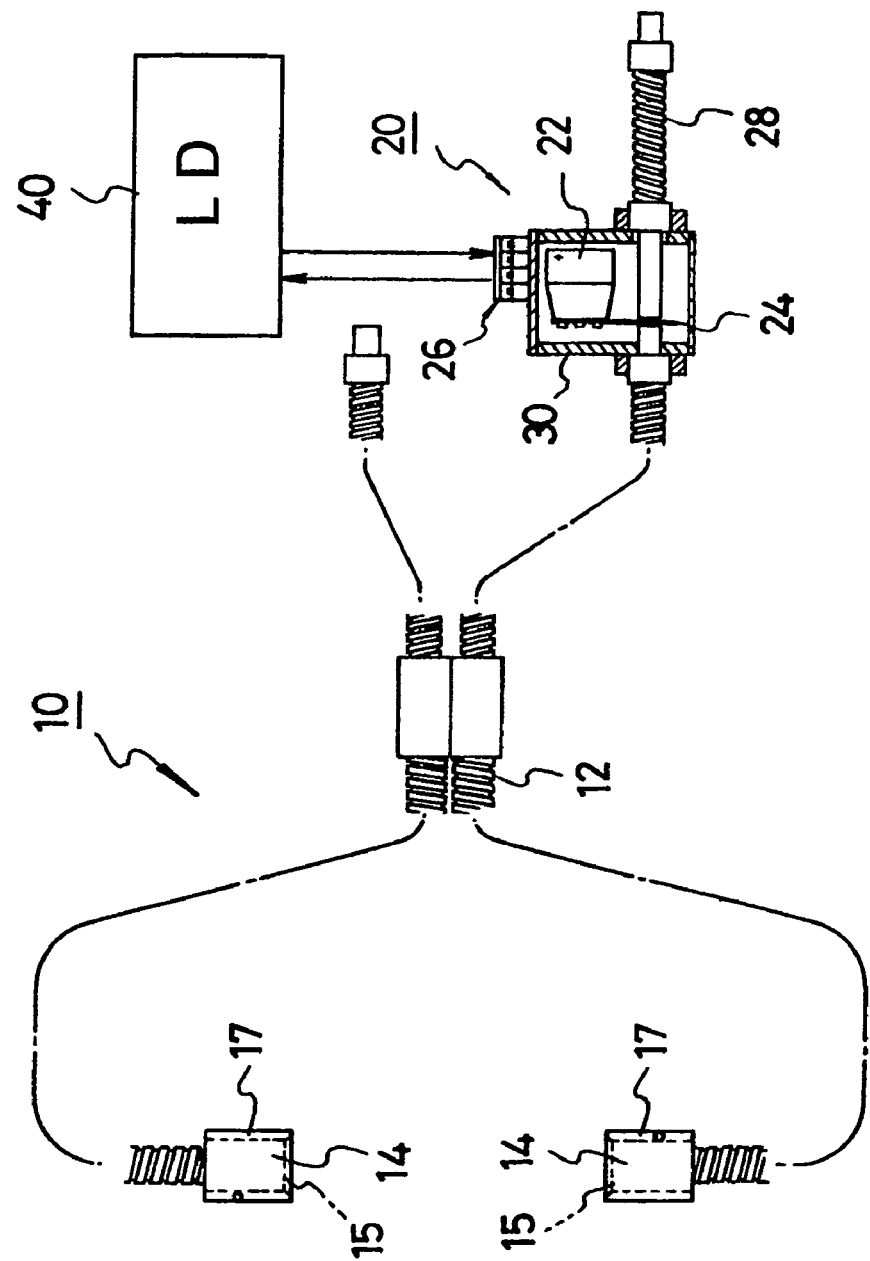
FIG. 1 is a top plan view showing the construction of an apparatus for measuring the internal qualities of fruits with a function of automatically controlling the intensity of light from a light source according to the present invention.
Figure 2A:
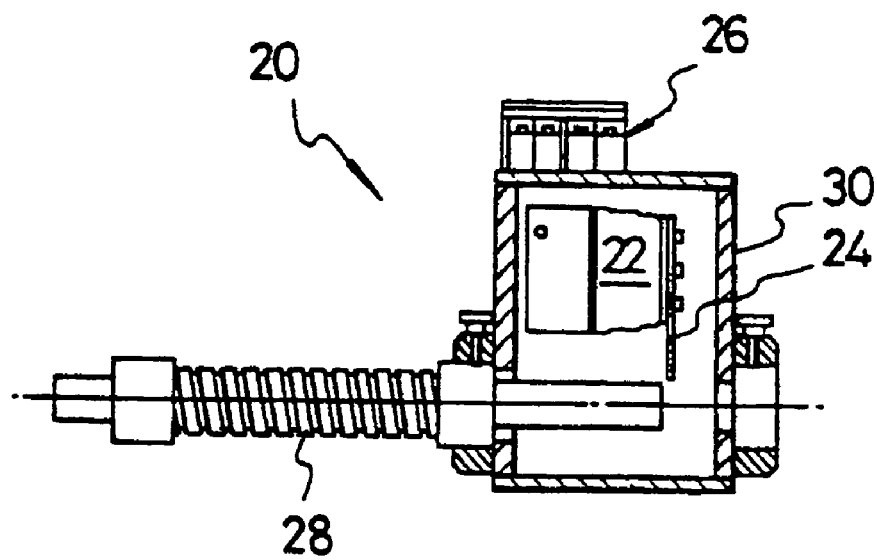
FIG. 2a is a top plan view of a light interrupting unit included in the apparatus of this invention when the unit measures both the intensity of light deflected by a sample and the intensity of light emitted from the light source.
Figure 2B:
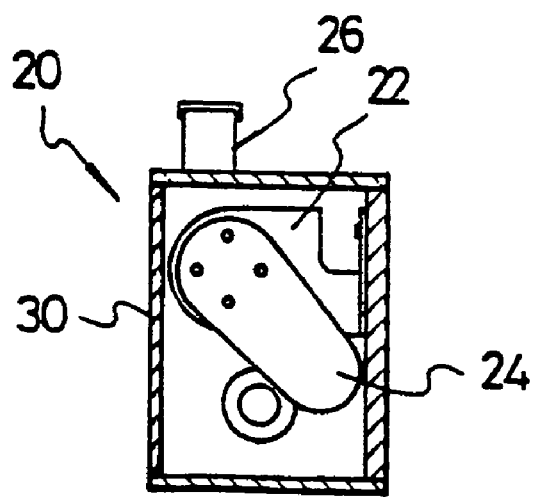
Figure 3A:
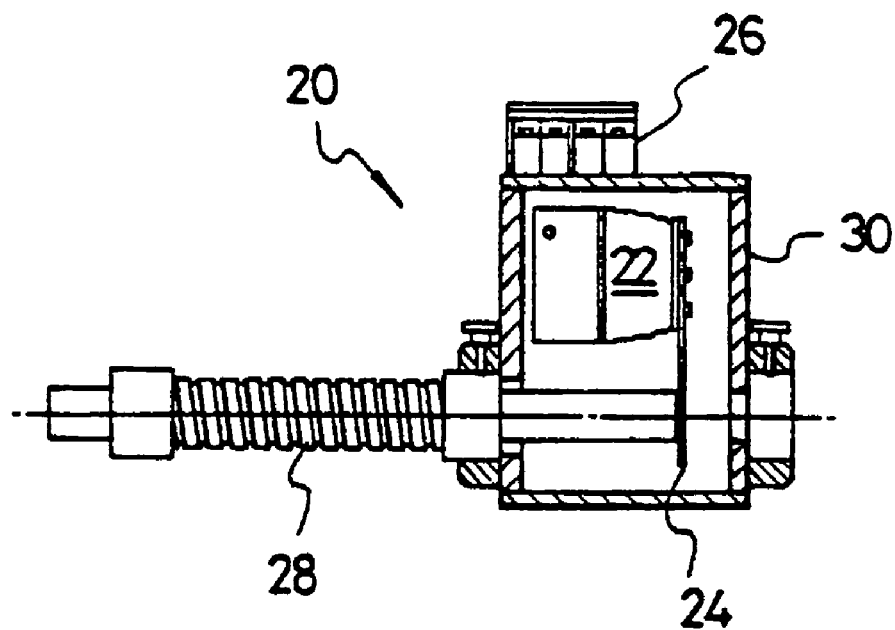
FIG. 3a is a top plan view of the light interrupting unit of this invention when it interrupts light emitted from the light source.
Figure 3B:
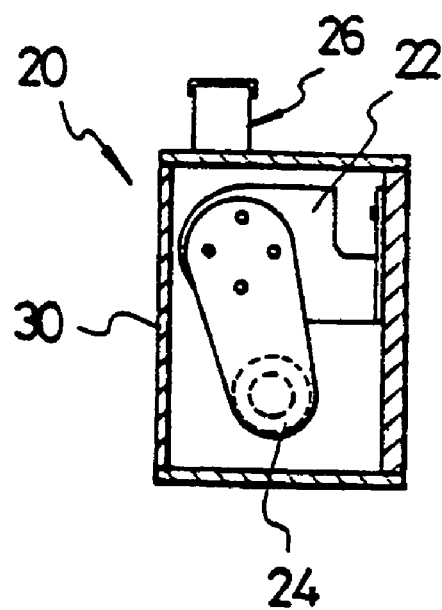

FIG. 1 is a top plan view showing the construction of an apparatus for measuring the internal qualities of fruits with a function of automatically controlling the intensity of light from a light source according to the present invention. FIG. 2a is a top plan view of a light interrupting unit included in the apparatus of this invention when the unit measures both the intensity of light deflected by a sample and the intensity of light emitted from the light source. FIG. 2b is a side sectional view of the light interrupting unit of FIG. 2a. FIG. 3a is a top plan view of the light interrupting unit of this invention when it interrupts light emitted from the light source. FIG. 3b is a side sectional view of the light interrupting unit of FIG. 3a.

As shown in FIG. 1, the apparatus of this invention is comprised of a bisected optical fiber bundle 10, a light interrupting unit 20, and a light detector (not shown).

As shown in FIG. 2, the optical fiber bundle 10 is comprised of two light guiding parts 12 guiding the light radiated from a light source to a desired position at which a fruit sample is laid. Two light radiating and receiving assemblies 14 are included in the optical fiber bundle 10 for radiating and receiving light guided through the light guiding parts 12 at a position near the fruit sample. The light guiding parts 12 each haves a concentric circular cross-section, with an optical fiber extending along the center of each light guide part 12. An outer circumference of the optical fiber is covered with a bellows pipe, which is flexible and desirably bent to form a desired light path. Between the light guiding parts 12 is installed a light interrupting unit 20 selectively interrupting the optical path of light radiated from the light source. Like the light guiding parts 12, each of the light radiating and receiving assemblies 14 takes a concentric circular cross-section. In each of the assembles 14, a light radiating part 15 for emitting light is placed at the central portion of each assembly 14, while a light receiving part 17 for receiving light is placed at the outside of the light radiating part 15.

The light interrupting unit 20, as shown in FIGS. 2a, 2b, 3a and 3b, is comprised of a solenoid actuator 22 operated with a power of 12V to repeatedly move at a predetermined rotational angle. A light interrupting board 24 is coupled to the solenoid actuator 22, and is rotated in conjunction with the actuator 22 to selectively interrupt light from the light source or allow the light to pass through the optical path. A power terminal 26 is included in the light interrupting unit 20 for applying electric power of 12V to the solenoid actuator 22. The light interrupting unit 20 also has a light guiding part 28 for guiding the transmitted light toward the light detector. The solenoid actuator 22 and the light interrupting board 24 are housed in a casing 30 of a rectangular shape, which is coupled to the light guiding part 28. The light guiding part 28 is partially positioned inside the casing 30, and has a naked optical fiber at its portion inside the casing 30.

The light detector is capable of calculating the intensity of light emitted from the light source and received by the light radiating and receiving assemblies 14, thus allowing analysis and interpretation of a spectrum for determination of the sweetness and acidity of fruits. If the intensity of the received light is reduced gradually, the light interrupting unit 20 is controlled to interrupt the light path from the light source.

The apparatus of this invention is operated as follows: The light emitted from the light source is bisected to pass through the light guiding parts 12 prior to being irradiated to a fruit sample laid in the light path formed by the light guiding parts 12. The inside of the light radiating and receiving assembly 14 positioned in each light guiding part 12 is mostly irradiated with the light directed toward the fruit sample, and the outside thereof receives the light deflected from the sample and acts as a sensor for transmitting the received light to a light detector (not shown). Then, the light detector calculates the deflection and transmission of the light from the fruit samples, with which the sweetness and the acidity of fruits are measured.

When there is placed a fruit sample in the light path, the deflected light from the sample is transmitted to the optical fiber extending to the light detector. When there is no sample, a large amount of light outputted from the light source is directly transmitted to the light detector through the light guiding parts 12, because the light radiating and receiving assemblies 14 are constructed to face each other. When the light outputted from the light source is directly transmitted to the light detector as described above, the detected signal is set as a high level reference signal, which is used in the conversion of the deflection ratio into a value for use in measuring the intensity of the deflected light.

When the light is deflected from a sample, or the light is directly transmitted without passing through any sample, both lights are transmitted to the light detector through the light interrupting unit 20.

That is, when the solenoid actuator 22 is turned off to open the light path as shown in FIGS. 2a and 2b, the lights deflected from the sample and emitted from the light source are both transmitted to the light detector. However, when the output of the light source is reduced or changed to a level lower than a predetermined level, the solenoid actuator 22 is operated to interrupt the light path with the light interrupting board 24, and interrupt the light radiated to the light detector. The light signal at this time is set as a low level reference signal or a blank signal.

As described above, the intensity, high level reference signal and low level reference signal of deflected light are automatically measured in a prompt manner by use of an electric signal. In the near infrared spectroscopy used in the present invention, the deflection "δ" of light is a value obtained from the following expression:

$$\delta = (\alpha - \gamma_1) / [(\beta \text{ or } \gamma_2) - \gamma_1]$$

wherein $\alpha$ is the intensity of light deflected from the sample $\beta$ is the intensity of light from the light source $\gamma_1$ is the low level reference signal $\gamma_2$ is the high level reference signal

INDUSTRIAL APPLICABILITY

As apparent from the above description, according to the present invention, opposite sides of a fruit sample are irradiated by near infrared rays, and the energy of lights deflected by the sample is measured and analyzed, thereby reducing an error in determining the sweetness of the fruits in addition to improving the accuracy of selection of fruits for determination of internal qualities of the fruits. As a result, troubles resulting from manual selection of fruits are overcome and the error in sweetness determination of fruits is greatly reduced. If this apparatus is used in an automated line, it greatly contributes to improving operational efficiency and precision of fruit selection and increasing operational reliability of a fruit selection system equipped with the apparatus.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

The invention claimed is:

1. An apparatus for measuring internal qualities of fruits with a function of automatically controlling the intensity of light from a light source, comprising:
    light guiding parts to guide light radiated from the light source to a position of a fruit sample to be measured;
    a light radiating and receiving assembly to radiate the light transmitted through the light guiding parts placed at a position near the fruit sample to fresh of the fruit sample so that the light is dispersed by the fresh of the fruit sample, and to receive the light deflected by the fresh of the fruit sample;
    a light interrupting unit installed between the light guiding parts coupled to the light radiating and receiving assembly which receives the light deflected by the fresh of the fruit sample, so as to selectively interrupt an optical path of the light deflected by the fresh of the fruit sample; and
    a light detector to calculate the intensity of light, radiated from the light source and received by the light radiating and receiving assembly, thus allowing analysis and interpretation of a spectrum for determination of sweetness and acidity of fruits, said light detector setting a detected signal, which is detected without any fruit sample, as a high level reference signal, and controlling the light interrupting unit to interrupt an optical path of light from the light source, thus setting a low level reference signal, when the intensity of the received light varies gradually.

2. The apparatus as set forth in claim 1, wherein the light interrupting unit is comprised of:
    a solenoid actuator operated with a power of 12V to repeatedly move at a predetermined rotational angle;
    a light interrupting board operated in conjunction with the solenoid actuator to selectively interrupt light from the light source or allow the light to pass through the optical path;
    a casing housing both the solenoid actuator and the light interrupting board;
    a power terminal provided outside the casing and applying electric power of 12V to said solenoid actuator; and
    a second light guiding part coupled to the casing, one side of which is exposed with an optical fiber so as to interrupt the light with the light interrupting board, and directing the light passing through it to the light detector.

* * * * *